US00PP13357P2

(12) United States Plant Patent
Grünewald

(10) Patent No.: US PP13,357 P2
(45) Date of Patent: Dec. 17, 2002

(54) TIBOUCHINA PLANT NAMED 'GRUE-TIB 01'

(76) Inventor: Theodorus P. M. Grünewald, Bergkampstrasse 27, 44534 Lünen (DE)

( * ) Notice: Subject to any disclaimer, the term of this patent is extended or adjusted under 35 U.S.C. 154(b) by 0 days.

(21) Appl. No.: 10/094,274

(22) Filed: Mar. 8, 2002

(51) Int. Cl.[7] ..... A01H 5/00
(52) U.S. Cl. ..... Plt./226
(58) Field of Search ..... Plt./226

(56) References Cited

U.S. PATENT DOCUMENTS

PP12,034 P2 * 8/2001 Masuda ..... Plt./226

OTHER PUBLICATIONS

UPOV ROM 2002/02 citation for 'Grue–TiB–02'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Tibouchina plant named 'Grue-TiB 01', characterized by its outwardly spreading and somewhat trailing plant habit; compact growth habit with short internodes; and purple-colored flowers.

1 Drawing Sheet

BOTANICAL CLASSIFICATION/CULTIVAR DESIGNATION

*Tibouchina organensis* cultivar Grue-TiB 01.

BACKGROUND OF THE INVENTION

The present Invention relates to a new and distinct cultivar of Tibouchina plant, botanically known as *Tibouchina organensis*, and hereinafter referred to by the name 'Grue-TiB 01'.

The new Tibouchina is a product of a induced mutation breeding program conducted by the Inventor in Lünen, Germany. The objective of the program is to create new Tibouchinas with different plant forms and sizes.

The new Tibouchina is an induced mutation of an unnamed selection of *Tibouchina organensis*, not patented. Mutations were induced by exposing unrooted cuttings of the unnamed Tibouchina selection to gamma radiation. The new Tibouchina was discovered and selected by the Inventor as a single flowering plant within a population of irradiated plants of the unnamed Tibouchina selection in 1999 in a controlled environment in Lünen, Germany. The new Tibouchina was selected on its plant form and growth habit.

Asexual reproduction of the new cultivar by cuttings taken in a controlled environment in Lünen, Germany since 1999, has shown that the unique features of this new Tibouchina are stable and reproduced true to type in successive generations.

SUMMARY OF THE INVENTION

Plants of the cultivar Grue-TiB 01 have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Grue-TiB 01'. These characteristics in combination distinguish 'Grue-TiB 01' as a new and distinct cultivar:

1. Outwardly spreading and somewhat trailing plant habit.
2. Compact growth habit with short internodes.
3. Purple-colored flowers.

In side-by-side comparisons conducted in Lünen, Germany, plants of the new Tibouchina differed from plants of the parent selection in the following characteristics:

1. Plants of the new Tibouchina were more outwardly spreading than plants of the parent selection.
2. Plants of the new Tibouchina were more compact than plants of the parent selection.
3. Plants of the new Tibouchina had smaller leaves than plants of the parent selection.
4. Plants of the new Tibouchina had smaller flowers than plants of the parent selection.

Compared to plants of the Tibouchina cultivar Grue-TiB 02, disclosed in U.S. Plant patent application Ser. No. 10/094,327, plants of the new Tibouchina are taller, have smaller leaves, and have larger flowers. Compared to plants of the Tibouchina cultivar Grue-TiB 03, disclosed in U.S. Plant patent application Ser. No. 10/094,336 plants of the new Tibouchina are larger, have larger flowers, and are more freely flowering. Compared to plants of the Tibouchina cultivar Grue-TiB 04, disclosed in U.S. Plant patent application Ser. No. 10/094,273, plants of the new Tibouchina are shorter, are not as freely branching, have smaller leaves, and are more freely flowering. Compared to plants of the Tibouchina cultivar Grue-TiB 05, disclosed in U.S. Plant patent application Ser. No. 10/094,334, plants of the new Tibouchina are shorter, are not as upright, and have smaller leaves.

Plants of the new Tibouchina can be compared to plants of the *Tibouchina urvilleana* Rich Blue Sun, not patented. In side-by-side comparisons conducted in Lünen, Germany, plants of the new Tibouchina differed from plants of the cultivar Rich Blue Sun in the following characteristics:

1. Plants of the new Tibouchina were more outwardly spreading and not as upright as plants of the cultivar Rich Blue Sun.

2. Plants of the new Tibouchina were more compact than plants of the cultivar Rich Blue Sun.

3. Plants of the new Tibouchina had smaller leaves than plants of the cultivar Rich Blue Sun.

4. Plants of the new Tibouchina had smaller flowers than plants of the cultivar Rich Blue Sun.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Tibouchina. The photograph comprises a top perspective view of a typical flowering plant of 'Grue-TiB 01'.

DETAILED BOTANICAL DESCRIPTION

Plants used for the aforementioned photograph and following observations and measurements were planted into 12-cm containers and grown for about six months during the summer and fall in a glass-covered greenhouse in Lünen, Germany. During the production of the plants, the day temperature ranged from 22 to 25° C. and night temperatures averaged 20° C. In the following description, color references are made to The Royal Horticultural Society Colour Chart, Edition 1995, except where general terms of ordinary dictionary significance are used.

Botanical classification: *Tibouchina organensis* cultivar Grue-TiB 01.

Parentage: Induced mutation of an unnamed selection of *Tibouchina organensis*, not patented.

Propagation:

*Type.*—By cuttings.

*Time to initiate roots.*—About 15 days at 20° C.

*Root description.*—Fine, freely branching.

Plant description:

*Form.*—Outwardly spreading and somewhat trailing plant habit; open form; subshrub. Appropriate for 12 to 17-cm containers. Moderately vigorous.

*Plant height.*—About 20 cm.

*Plant diameter.*—About 40 cm.

*Lateral branches.*—Quantity per plant: About 3 to 5. Length: About 30 cm. Diameter: About 3 mm. Internode length: About 1 to 4 cm. Strength: Strong. Texture: Pubescent. Color: Immature: 146C. Mature: Woody, 199D.

*Foliage description.*—Arrangement: Opposite, simple. Quantity of leaves per lateral branch: About 30. Length, largest leaves: About 6 cm. Width, largest leaves: About 2.8 cm. Shape: Lanceolate. Apex: Acuminate. Base: Obtuse, rounded. Margin: Entire. Texture, upper and lower surfaces: Pubescent. Venation pattern: Parallel. Petiole length: about 4 to 10 mm. Petiole diameter: About 2.5 mm. Color: Young and fully expanded foliage, upper surface: 147A. Young and fully expanded foliage, lower surface: 147B. Venation, upper surface: 147B. Venation, lower surface: 147C. Petiole, upper and lower surfaces: 147C.

Flower description:

*Flower type and habit.*—Rotate flowers solitary or arranged in terminal or axillary panicles, typically three flowers per panicle; about 10 to 20 flowers per lateral branch will develop during the flowering period. Flowers and flowers face mostly outward. Flowers not persistent.

*Natural flowering season.*—In the northern hemisphere, plants flower during the summer and autumn; flowering recurrent during this period.

*Flower longevity on the plant.*—About one day.

*Fragrance.*—None detected.

*Flowers.*—Diameter: About 8.5 cm. Depth (height): About 3.5 cm.

*Flower buds (before showing color).*—Length: About 2.1 cm. Diameter: About 9 mm. Shape: Roughly ovoid. Color: 144B.

*Petals.*—Arrangement: Four to five petals in a single whorl. Length: About 4.4 cm. Width: About 3.6 cm. Shape: Obovate. Apex: Rounded. Base: Cuneate. Margin: Entire. Texture, upper and lower surfaces: Smooth, satiny. Color: When opening, upper surface: 89C. When opening, lower surface: 89D. Fully opened, upper surface: 90B. Fully opened, lower surface: 90C.

*Sepals.*—Arrangement: Four to five sepals in a single whorl. Length: About 1.3 cm. Diameter: About 4.5 mm. Shape: Lanceolate. Apex: Apiculate. Base: Cuneate. Texture, upper and lower surfaces: Pubescent. Color, upper and lower surfaces: 145C.

*Peduncles.*—Length: About 2.5 mm. Diameter: About 5 mm. Strength: Strong. Texture: Pubescent. Color: 145C.

*Reproductive organs.*—Stamens: Quantity per flower: About eight to ten. Filament length: About 2.4 cm. Filament color: 83B. Anther length: About 1.4 cm. Another color: Darker than 89A. Pollen: None observed. Pistils: Quantity per flower: One. Style length: About 3.5 cm. Style color: 83B. Stigma shape: Round. Stigma color: 155C. Ovary color: 149D.

*Seed/fruit.*—Seed nor fruit production has not been observed.

Disease/pest resistance: Plants of the new Tibouchina have not been noted to be resistant to pathogens or pests common to Tibouchina.

It is claimed:

1. A new and distinct cultivar of Tibouchina plant named 'Grue-TiB 01', as illustrated and described.

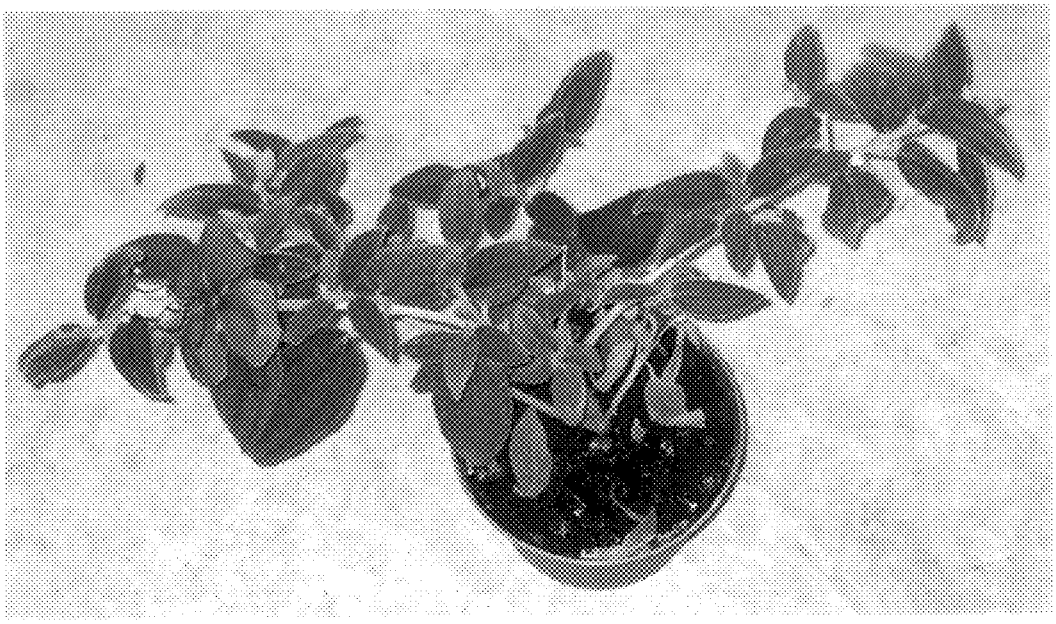

* * * * *